(12) United States Patent
Shi

(10) Patent No.: US 8,445,435 B2
(45) Date of Patent: May 21, 2013

(54) MAST CELL STABILIZERS IN THE TREATMENT OF OBESITY

(75) Inventor: Guo-Ping Shi, Newton, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 143 days.

(21) Appl. No.: 12/232,789

(22) Filed: Sep. 24, 2008

(65) Prior Publication Data
US 2009/0093511 A1 Apr. 9, 2009

Related U.S. Application Data

(60) Provisional application No. 60/960,408, filed on Sep. 28, 2007.

(51) Int. Cl.
| | | |
|---|---|---|
| A01N 43/42 | (2006.01) | |
| A01N 43/16 | (2006.01) | |
| A01N 43/40 | (2006.01) | |
| A61K 31/44 | (2006.01) | |
| A61K 31/35 | (2006.01) | |
| A61K 31/445 | (2006.01) | |
| A61K 38/18 | (2006.01) | |
| C07K 14/51 | (2006.01) | |

(52) U.S. Cl.
USPC ............. 514/8.8; 514/291; 514/324; 514/456

(58) Field of Classification Search
None
See application file for complete search history.

(56) References Cited

U.S. PATENT DOCUMENTS

| | | | |
|---|---|---|---|
| 4,634,699 | A | 1/1987 | McDermed |
| 4,871,865 | A | 10/1989 | Lever |
| 4,923,892 | A | 5/1990 | Lever |
| 5,780,461 | A | 7/1998 | Heath, Jr. |
| 6,207,684 | B1 | 3/2001 | Aberg |
| 6,225,327 | B1 | 5/2001 | Miller |
| 6,232,297 | B1 | 5/2001 | Linden |
| 6,414,027 | B1 | 7/2002 | Neal |
| 6,777,429 | B1 | 8/2004 | Adam et al. |
| 7,060,827 | B2 | 6/2006 | Singh |
| 7,271,266 | B2 | 9/2007 | Finke et al. |
| 2001/0009917 | A1 | 7/2001 | Gray |
| 2004/0092511 | A1 | 5/2004 | Billstein et al. |
| 2004/0259925 | A1 | 12/2004 | Riedel |
| 2004/0259952 | A1* | 12/2004 | Abbas et al. ........ 514/571 |
| 2005/0182103 | A1 | 8/2005 | Finke et al. |
| 2006/0127511 | A1 | 6/2006 | Tripp |
| 2006/0263350 | A1 | 11/2006 | Lane |
| 2006/0280788 | A1 | 12/2006 | Casey et al. |
| 2007/0244185 | A1 | 10/2007 | Hanko |
| 2008/0027111 | A1* | 1/2008 | Shi .................... 514/336 |

FOREIGN PATENT DOCUMENTS
WO   WO/2008/013799 A2   1/2008

OTHER PUBLICATIONS

Friedman et al. Leptin and the regulation of body weight in mammals. Nature. vol. 395, 1996.*

International Search Report for PCT/US2008/011026 filed Sep. 24, 2008.
Written Opinion of the International Searching Authority for PCT/US2008/011026 filed Sep. 24, 2008.
Bingham, et al., "Mast-Cell Responses in the Development of Asthma," *J. Allergy Clin. Immunol.* 105:S527-S534 (Feb. 2000).
Brakenhielm, et al., "Angiogenesis in Adipose Tissue," *Methods in Mol. Biol.* 456:65-81 (Jun. 2008).
Cannon, et al., "Brown Adipose Tissue: Function and Physiological Significance," *Physiol. Rev.* 84:277-359 (Jan. 2004).
Coussens, et al., "Inflammatory Mast Cells Up-Regulate Angiogenesis During Squamous Epithelial Carcinogenesis," *Genes Dev.* 13:1382-1397 (1999).
Crandall, et al., "A Review of the Microcirculation of Adipose Tissue: Anatomic, Metabolic, and Angiogenic Perspectives," *Microcirculation* 4(2):211-232 (1997).
Daugherty, et al., "Mechanisms of Abdominal Aortic Aneurysm Formation," *Curr. Atheroscler. Rep.* 4:222-227 (2002).
Duttlinger, et al., "The $W^{sh}$ and Ph Mutations Affect the c-kit Expression Profile: c-kit Misexpression in Embryogenesis Impairs Melanogenesis in $W^{sh}$ and Ph Mutant Mice," *Proc. Natl. Acad. Sci. USA* 92:3754-3758 (Apr. 1995).
Eigen, et al., "Evaluation of the Addition of Cromolyn Sodium to Bronchodilator Maintenance Therapy in the Long-Term Management of Asthma," *J. Allergy Clin. Immunol.* 80(4):612-621 (1987).
Fantuzzi, et al., "Adipose Tissue, Adipokines, and Inflammation," *J. Allergy Clin. Immunol.* 115:911-919 (May 2005).
Galli, et al., "Mast Cells in the Development of Adaptive Immune Responses," *Nat. Immunol.* 6(2):135-142 (Feb. 2005).
Inoue, et al., "Human Mast Cell Basic Fibroblast Growth Factor in Pulmonary Fibrotic Disorders," *Am. J. Pathol.* 149:2037-2054 (Dec. 1996).
Kintscher, et al., "T-lymphocyte Infiltration in Visceral Adipose Tissue," *Arterioscler. Thromb. Vasc. Biol.* 28:1304-1310 (Apr. 2008).
Koban, et al., "Chronic REM-Sleep Deprivation of Rats Elevates Metabolic Rate and Increases UCP1 Gene Expression in Brown Adipose Tissue," *Am. J. Physiol. Endocrinot Metab.* 289:E68-E74 (Jul. 2005).
Lee, et al., "Mast Cells: A Cellular Link Between Autoantibodies and Inflammatory Arthritis," *Science* 297:1689-1692 (Sep. 2002).
Lätti, et al., "Mast Cell-Mediated Apoptosis of Endothelial Cells in Vitro: A Paracrine Mechanism Involving TNF-α-Mediated Down-Regulation of bcl-2 Expression," *J. Cell. Physiol.* 195:130-138 (2003).
Leskinen, et al., "Mast Cell Chymase Induces Smooth Muscle Cell Apoptosis by a Mechanism Involving Fibronectin Degradation and Disruption of Focal Adhesions," *Arterioscler. Thromb. Vasc. Biol.* 23:238-243 (2003).
Leskinen, et al., "Regulation of Smooth Muscle Cell Growth, Function and Death in Vitro by Activated Mast Cells: a Potential Mechanism for the Weakening and Rupture of Atherosclerotic Plaques,"*Biochem. Pharmacol.* 66:1493-1498 (2003).

(Continued)

*Primary Examiner* — Anna Pagonakis

(74) *Attorney, Agent, or Firm* — Law Office of: Michael A. Sanzo, LLC

(57) ABSTRACT

The present invention is directed to methods of treating or preventing the development of obesity by administering compounds that stabilize mast cells. In addition, it includes pharmaceutical compositions which have both a mast cell stabilizer and instructions regarding the use of the stabilizer in treating or preventing obesity.

6 Claims, No Drawings

OTHER PUBLICATIONS

Mekori, et al., "Molecular Mechanisms in Allergy and Clinical Immunology," *J. Allergy Clin. Immunol.* 104:517-523 (Sep. 1999).

Mueller, et al., "Measurement of Platelet-Activating Factor in a Canine Model of Coronary Thrombosis and in Endarterectomy Samples from Patients with Advanced Coronary Artery Disease," *Circ. Res.* 77:54-63 (1995).

Pang, et al., "Macrophage Infiltration into Adipose Tissue May Promote Angiogenesis for Adipose Tissue Remodeling in Obesity," *Am. J. Physiol. Endocrinol. Metab.* 295:E313-E322 (May 2008).

Robbie-Ryan, et al., "The Role of Mast Cells in Allergy and Autoimmunity," *Curr. Opin. Immunol.* 14:728-733 (2002).

Rocha, et al., "Interferon-γ, a Th1 Cytokine, Regulates Fat Inflammation: A Role for Adaptive Immunity in Obesity," *Circ. Res.* 103:467-476 (Aug. 2008).

Rupnick, et al., "Adipose Tissue Mass can be Regulated Through the Vasculature," *Proc. Natl. Acad. Sci. USA* 99(16):10730-10735 )Aug. 2002).

Schwartz, et al., "Structure and Function of the Chemical Mediators of Mast Cells," *Prog. Allergy* 34:271-321 (1984).

Secor, et al., Mast Cells Are Essential for Early Onset and Severe Disease in a Murine Model of Multiple Sclerosis, *J. Exp. Med.* 191:813-822 (Mar. 2000).

Shepherd, et al., "Adipose Cell Hyperplasia and Enhanced Glucose Disposal in Transgenic Mice Overexpressing GLUT4 Selectivity in Adipose Tissue," *J. Biol. Chem.* 268:22243-22246 (1993).

Shi, et al., "Molecular Cloning and Expression of Human Alveolar Macrophage Cathepsin S, an Elastinolytic Cysteine Protease," *J. Biol. Chem.* 267:7258-7262 (Apr. 1992).

Skoura, et al., "Essential Role of Sphingosine 1-Phosphate Receptor 2 in Pathological Angiogenesis of the Mouse Retina," *J. Clin. Invest.* 117(9):250602516 (Sep. 2007).

Sun, et al., Mast Cells Modulate the Pathogenesis of Elastase-Induced Abdominal Aortic Aneurysms in Mice, *J. Clin. Invest.* 117(11):3359-3368 (Nov. 2007).

Sun, et al., "Mast Cells Promote Atherosclerosis by Releasing Proinflammatory Cytokines," *Nat. Med.* 13(6):719-724 (Jun. 2007).

Taleb, et al., Cathepsin S Promotes Human Preadipocyte Differentiation: Possible Involvement of Fibronectin Degradation, *Endocrinology* 147(10):4950-4959 (Oct. 2006).

Toda, et al., "Mechanism of Histamine Actions in Human Coronary Arteries," *Circ. Res.* 61:280-286 (Aug. 1987).

Wang, et al., "Cathespsin S Controls Angiogenesis and Tumor Growth via Matrix-Derived Angiogenic Factors," *J. Biol. Chem.* 281:6020-6029 (Mar. 2006).

Weisberg, et al., "Obesity is Associated with Macrophage Accumulation in Adipose Tissue," *J. Clin. Invest.* 112(12):1796-1808 (Dec. 2003).

Wild, et al., "Quantitative Assessment of Angiogenesis and Tumor Vessel Architecture by Computer-Assisted Digital Image Analysis: Effects of VEGF-Toxin Conjugate on Tumor Microvessel Density," *Microvasc. Res.* 59:368-376 (2000).

Wolters, et al., "Tissue-Selective Mast Cell Reconstruction and Differential Lung Gene Expression in Mast Cell-Deficient $Kit^{W-sh}/Kit^{W-sh}$ Sash Mice," *Clin. Exp. Allergy* 35:82-88 (2005).

Wu, et al., "T-Cell Accumulation and Regulated on Activation, Normal T Cell Expressed and Secreted Upregulation in Adipose Tissue in Obesity," *Circulation* 115:1029-1038 (Feb. 2007).

Xu, et al., "Proteolytic Exposure of a Site Within Collagen Type IV is Required for Angiogenesis and Tumor Growth in Vivo," *J. Cell Biol.* 154:1069-1079 (2001).

Yang, et al., "Cathepsin L Activity Controls Adipogenesis and Glucose Tolerance," *Nat. Cell Biol.* 9(8):970-977 (Aug. 2007).

Zudaire, et al., "Adrenomedullin is a Cross-Talk Molecule that Regulates Tumor and Mast Cell Function During Human Carcinogenesis," *Am. J. Pathol.* 168:280-291 (Jan. 2006).

The Merck Manual of Diagnosis and Therapy [online]. Whitehouse Station, N.J., USA, Merck & Co. Inc. 2005 [retrieved on Jul. 30, 2007], Retrieved from internet:<http://www.merck.com/mmpe/print/sec07/ch073/ch073a.html>.

Clarke, et al., "A Comparison of the Efficacy of Ketotifen (HC20-511) with Sodium Cromoglycate (SCG) in Skin Test Positive Asthma," *Br. J. Clin. Pharmac.* 10:473-476 (1980).

Geoffrey, et al., "Evidence of a Functional Role for Mast Cells in the Development of Type 1 Diabetes Mellitus in the BioBreeding Rat," *J. Immunol.* 177:7275-7286 (2006).

Liu, et al., "Genetic deficiency and pharmacological stabilization of mast cells reduce diet-induced obesity and diabetes in mice," *Nature Medicine* 15:940-945 (2009), with supplementary figures and tables attached.

International Preliminary Report on Patentability for PCT/US2008/011026 filed Sep. 24, 2008.

Coffee, et al., "Peroxynitrate-Induced Nitrotyrosination of Proteins is Blocked by Direct 5-Lipoxygenase Inhibitor Zileuton," *J. Pharmacol. Exp. Ther.* 299:198-203 (Apr. 2001).

Constantinides, et al., "Mast Cells and Susceptibility to Experimental Atherosclerosis," *Science* 117:505-506 (1953).

Cuzzocrea, et al., "5-Lipoxygenase modulates colitis through the regulation of adhesion molecule expression and neutrophil migration," *Lab. Invest.* 85:808-822 (Apr. 2005).

Daugherty, et al., "Mouse Models of Abdominal Aortic Aneurysms," *Arterioscler. Thromb. Vasc. Biol.* 24:429-434 (2004).

Faleiro, et al., "Cerebral Vasopasm: Presence of Mast Cells in Human Cerebral Arteries After Aneurysm Rupture," *Neurosurg.* 54:733-735 (Jun. 1981).

Johnson, et al., "Activation of Matrix-Degrading Metalloproteinases by Mast Cell Proteases in Atherosclerotic Plaques," *Thromb. Vasc. Biol.* 18:1707-1715 (Nov. 1998).

Kovanen, et al., "Infiltrates of Activated Mast Cells at the Site of Coronary Atheromatous Erosion or Rupture in Myocardial Infarction," *Circulation* 92:1084-1088 (1995).

Li, et al., "Oxygen-Glucose Deprivation Activates 5-Lipoxygenase Mediated by Oxidative Stress Through the p38 Mitogen-Activated Protein Kinase Pathway in PC12 Cells,"*J. Neurosci. Res.* 87:991-1001 (Feb. 2009).

Pyo, et al., "Targeted Gene Disruption of Matrix Metalloproteinase-9 (Gelatinase B) Suppresses Development of Experimental Abdominal Aortic Aneurysms," *J. Clin. Invest.* 105:1641-1649 (Jun. 2000).

Rao, et al., "Anti-Inflammatory Activity of a Potent, Selective Leukotriene $A_4$ Hydrolase Inhibitor in Comparison with the 5-Lipoxygenase Inhibitor Zileuton," *J. Pharmacol. Exp. Therapeutics* 321:1154-1160 (Mar. 2009).

Shi et al., "Cathepsin S Required for Normal MHC Class II Peptide Loading and Germinal Center Development," *Immunity* 10:197-206 (Feb. 1999).

SHi, et al., "Deficiency of the Cysteine Protease Cathepsin S Impairs Microvessel Growth," *Circ. Res.* 92:493-500 (Mar. 2003).

Shi, et al., "Cystatin C Deficiency in Human Atherosclerosis and Aortic Aneurysms," *J. Clin. Invest.* 104:1191-1197 (Nov. 1999).

Ward, et al., "Isoform-specific phosphoinositide 3-kinase inhibitors as therapeutic agents," *Current Opinion in Pharmacology* 3:426-434 (2003).

Zouboulis, et al., "Zileuton, an Oral 5-Lipoxygenase Inhibitor, Directly Reduces Sebum Production," *Dermatology* 210:36-38 (Jan. 2005).

NIH Heart and Stroke Research: Fact Sheet, American Heart Association, 2004.

Cardiovascular Disease: Treatment for Stroke, Stanford Hospital & Clinics, 2003.

Supplemental European Search Report for EP 08 83 5091 corresponding to PCT/US2008/011026 completed on Apr. 27, 2012, mailed on May 14, 2012 and posted on the Euopean Patent Register on the mail date or thereabouts.

Avenell, et al., "What interventions should we add to weight reducing diets in adults with obesity? a systematic review of randomized controlled trails of adding drug therapy, exercise, behaviour therapy or combinations of these interventions," *J. Hum. Nutr. Dietet.* 17(4):293-316 (2004).

Database Medline; NLM149739669; XP-002674853; Schwarzer, et al., "Ketotifen alone or as additional medication for long-term control of asthma and wheeze in children" (2004).

\* cited by examiner

MAST CELL STABILIZERS IN THE TREATMENT OF OBESITY

CROSS REFERENCE TO RELATED APPLICATIONS

The present application claims priority to and the benefit of U.S. provisional application 60/960,408, filed on Sep. 28, 2007 which is hereby incorporated herein by reference in its entirety.

STATEMENT OF GOVERNMENT FUNDING

The United States Government has a paid-up license in this invention and the right in limited circumstances to require the patent owner to license others under reasonable terms as provided for by the terms of NIH grant HL60942, awarded by the Department of Health and Human Services.

FIELD OF THE INVENTION

The present invention is directed to compositions and methods that are useful in the treatment and prevention of obesity.

BACKGROUND OF THE INVENTION

Obesity, an extremely common and detrimental metabolic disease, poses serious threats to the public health both in the US and worldwide. The prevalence of this disorder has markedly increased since the mid-1980s. In the United States, 50% of adults are overweight and 30% are obese. Even more seriously, the prevalence of obesity and associated diabetes are increasing rapidly in children. The impact of obesity on the individual, the family, and society, especially with respect to the cost and utilization of health care resources, is very serious. Therefore, controlling body weight is not just a scientific topic but also a matter of growing social concern.

Mast cells (MCs) help induce an allergic response by releasing cytoplasmic granules, whose contents promote allergic inflammation upon sensitization by IgE or complement factors (Schwartz, et al., *Prog. Allergy* 34:271-321 (1984); Mekori, et al., *J. Allergy Clin. Immunol.* 104:517-523 (1999)). Recent biochemical and histological observations suggest that MCs may also participate in blood-borne leukocyte recruitment (Mekori, et al., *J. Allergy Clin. Immunol.* 104:517-523 (1999)), smooth muscle cell (SMC)/endothelial cell (EC) proliferation (Toda, N., *Circ. Res.* 61:280-286 (1987); Inoue, et al., *Am. J. Pathol.* 149:2037-2054 (1996); Mueller, et al., *Circ. Res.* 77:54-63 (1995)), apoptosis (Latti, et al., *J. Cell. Physiol.* 195:130-138 (2003); Leskinen, et al., *Arterioscler. Thromb. Vasc. Biol.* 23:238-2343 (2003); Leskinen, et al., *Biochem. Pharmacol.* 66:1493-1498 (2003)), T-lymphocyte migration and activation (Mekori, et al., *J. Allergy Clin. Immunol.* 104:517-23 (1999)), angiogenesis (Zudaire et al., *Am. J. Pathol.* 168:280-291 (2006)), and matrix remodeling (Daugherty, et al., *Curr. Atheroscler. Rep.* 4:222-227 (2002)). To date, a clear role for mast cells with respect to obesity has not been determined.

The discovery of mast cell-null mice (Duttlinger, et al., *Proc. Natl. Acad. Sci. USA* 92:3754-3758 (1995); Wolters, et al., *Clin. Exp Allergy* 35:82-88 (2005)) and the availability of obesity models (both genetic and diet-induced obese mice) have now made it possible to assess the role of mast cells in obesity and its complications. In addition, the availability of gene knockout mice for important mast cell mediators or white adipose tissue (WAT) chemokine receptors makes it possible to identify the mediators in mast cells that are essential for obesity and the chemokines in WAT that are required for mast cell homing.

SUMMARY OF THE INVENTION

The present invention is based upon experiments suggesting that mast cells play an important role in the development of obesity, probably due to the manufacture and release of proinflammatory cytokines and other mediators. Mice lacking mast cells gain substantially less weight than their normal counterparts when fed a Western diet. However, if the normal mice are also administered a mast cell stabilizer, weight gain is substantially avoided.

In its first aspect, the invention is directed to a method for treating or preventing obesity in either an animal or human by administering an effective amount of a drug that stabilizes mast cells. The term "effective amount" refers to a sufficient quantity of drug to achieve a therapeutic objective. In the present case, this means that a sufficient amount of mast cell stabilizer must be given to promote weight loss, when given as a treatment for obesity, or to prevent weight gain, when given to prevent the development of obesity. If the drug is delivered nasally, the typical dosage will be between 5 and 100 mg per day. If given orally, the dosage will be somewhat higher, typically 50-1500 mg per day. For the purposes of the present invention, a person or animal is considered obese if they are more than 20% heavier than their ideal body weight, have a body mass index (BMI) of 30 or higher and/or have more than 30% body fat.

The mast cell stabilizing drug that is administered in the method described above will preferably be divided into two or more equal doses given over a 24 hour period. Preferred drugs are cromolyn, nedocromil, ketotifen and lodoxamide. These may be given in any pharmaceutically acceptable form, including pharmaceutically acceptable salts, such as sodium, disodium, potassium or lithium salts. It will be understood that, unless otherwise indicated, reference to one of these drugs includes all of its pharmaceutically acceptable forms. Some preferred forms are: nedocromil sodium (especially at 5-50 mg per day when delivered nasally or 50-500 mg per day when delivered orally); ketotifen fumarate (especially when delivered orally at 1-200 mg per day) and lodoxamide tromethamine (especially when delivered orally at 1-200 mg per day). The most preferred drug is cromolyn sodium or disodium, administered orally at a dosage of 200-1,000 mg per day. All dosages mentioned herein are with respect to the administration of drugs to humans. If the drugs are administered to an animal, the dosage for humans may be used to provide guidance and an adjustment made for difference in weight. For example, an animal weighing about 50 lbs would receive about one third of the dose of a human.

The method described above may be performed to either promote weight loss in an individual that is obese or prevent weight gain in an individual, especially an individual that is prone to weight gain due to genetic or environmental factors. When given to a human or animal treat obesity, drug administration should be continued on a daily basis until an individual has lost at least 10%, and preferably 15 or 20%, of their original weight. In a particularly preferred embodiment, obese individuals will be administered cromolyn, particularly cromolyn sodium or disodium, at a dose of about 200-1,000 mg daily for this duration. Patients that are treated may have other conditions besides obesity or they may be free of conditions such as allergies, cardiovascular disease or diabetes at the time of treatment.

In another aspect, the invention is directed to a therapeutic composition having both a mast cell stabilizer and instructions for administering this stabilizer to a patient to prevent or treat obesity. The stabilizer should be part of a pharmaceutical composition in unit dose form and be packaged in a finished pharmaceutical container. The term "unit dose form" refers to a single drug administration entity, such as a tablet, capsule, or quantity of solution. A "finished pharmaceutical container" refers to any of the different types of packaging typically used for pharmaceuticals such as bottles, vials, blister packs, etc. For the purposes of the present invention, a finished pharmaceutical container will include packaging designed for the nasal administration of drugs, i.e., bottles or vials that contain, and can be used to deliver, a solution or powder as a nasal spray. Similarly, a "unit dose form" will include a solution in which drug is dissolved at a concentration that provides a therapeutic effect when administered to a patient nasally or orally in a fixed amount.

The most preferred mast cell stabilizers for inclusion in the therapeutic compositions are cromolyn, nedocromil, ketotifen and lodoxamide. When these drugs are given orally in the form of a tablet or capsule, a unit dose will typically be between 5 and 1,000 mg and more typically between 10 and 500 mg. An equivalent amount would be in a unit dose form administered as an oral solution. If the drugs are given nasally, then solutions should typically contain a sufficient concentration of drug so that a patient receives between 0.1 and 10 mg per spray.

The instructions that form a part of the therapeutic composition may appear on packaging containing the mast cell stabilizer, on the finished pharmaceutical container or as a separate package insert. The instructions will include the dosage of mast cell stabilizer that should be administered to a patient, e.g., to treat or prevent obesity. The patients indicated for treatment will typically be patients that are obese, have previously been obese, have a family history of obesity or be patients in which weight gain would create especially severe health risks, e.g., patients with established cardiovascular disease.

The invention also includes methods for determining whether a particular compound will be useful as a treatment or preventative for obesity by assaying the compound for its ability to stabilize mast cells. Any of the stabilization assays that are known in the art, particularly those developed to screen compounds for usefulness in the treatment of allergies, may be used for this purpose.

DETAILED DESCRIPTION OF THE INVENTION

The present invention is based upon the experiments summarized below in the Examples section which indicate that mast cell stabilizers can be used to control obesity. These drugs may be taken to either help obese people lose weight or to prevent people from becoming obese.

A. Mast Cell Stabilizers

Drugs that stabilize mast cells have been studied extensively in connection with the treatment of allergies and several of these drugs are available commercially. The most preferred mast cell stabilizers are cromolyn, nedocromil, ketotifen and lodoxamide and may either be purchased or synthesized using methods well known in the art. In addition, any of the other pharmaceutically acceptable mast cell inhibitors described in the art may be used in the invention. These include compounds disclosed in U.S. Pat. Nos. 6,207,684; 4,634,699; 6,207,684; 4,871,865; 4,923,892; 6,225,327; and 7,060,827. Methods for preparing the compounds are presented in each of the U.S. patents along with information on how the compounds may be purified and the forms in which they may be used. These compounds may be given to patients in any pharmaceutically acceptable form, including any pharmaceutically acceptable salt, with the most preferred drug being either sodium or disodium cromolyn.

B. Making of Pharmaceutical Compositions

Mast cell stabilizing drugs may be incorporated into pharmaceutical compositions in accordance with methods that are standard in the art (see e.g., *Remington's Pharmaceutical Sciences*, Mack Publishing Co., (1990)). Formulations may be designed for delivery by any of the routes commonly used in the art, with preparations designed for oral or nasal delivery being preferred. For oral compositions, e.g. tablets or capsules, the mast cell stabilizing drug should typically be present in an amount of between 1 and 500 mg. In compositions for nasal delivery, stabilizers should typically be present at 0.5 mg/ml-50 mg/ml and more preferably at 1 mg/ml-20 mg/ml. Similar concentration ranges may be used in solutions to be taken orally. Although not preferred, other routes of administration may also be employed.

Mast cell stabilizers may be used in conjunction with any of the vehicles and excipients commonly employed in pharmaceutical preparations including water, salt solutions, alcohols, gum arabic, vegetable oils, benzo-alcohols, polyethylene glycol, gelatin, carbohydrates such as lactose, amylase, or starch; magnesium stearate; talc; salycic acid; paraffin; fatty acid esters; polymers; etc. The pharmaceutical preparations can be sterilized and, if desired, mixed with auxiliary agents such as: dispersants; lubricants; preservatives; stabilizers; wetting agents; emulsifiers; salts for influencing osmotic pressure; buffers; coloring agents; flavoring agents; and/or aromatic substances.

Solutions, particularly solutions for injection, can be prepared using water or physiologically compatible organic solvents such ethanol, 1,2-propylene glycol; polygycols; dimethylsulfoxides; fatty alcohols; triglycerides; partial esters of glycerine; and the like. The preparations can be made using conventional techniques and may include sterile isotonic saline, water, 1,3-butanediol, ethanol, 1,2-propylene glycol, polygycols mixed with water, ringers Ringer's solution etc.

C. Dosage Forms and Routes of Administration

The present invention is compatible with any route of administration including oral, peroral, internal, rectal nasal, lingual, transdermal, vaginal, intravenous, intraarterial, intramuscular, intraperitoneal, intracutaneus and subtaneous routes. Dosage forms that may be used include tablets, capsules, powders, aerosols, suppositories, skin patches, parenterals, sustained release preparations and oral liquids, including suspensions solutions and emulsions. The most preferred routes for administration are oral and nasal. If desired, compositions, particularly compositions for injection, may be freeze-dried and lyophilizates reconstituted before administration. Dosage forms may include mast cell stabilizers as the sole active ingredient or they may include other active agents as well. All dosage forms may be prepared using methods that are standard in the art and that are taught in reference works such as *Remington's Pharmaceutical Sciences* (Osol A ed., Mack Publishing Co. (1990)).

D. Treatment Methods

The therapeutic objective of the methods described herein will be to reduce the weight of a patient or to prevent the further weight gain. When used to prevent weight gain optimal dosages will be based upon the results of animal studies, e.g., such as those described herein, and clinical studies performed using methods well known in the art. Mast cell stabilizing drugs are already available for the treatment of other conditions, particularly allergies, and existing dosages may serve as a starting point for evaluating dosages effective in preventing or treating obesity. Based upon existing knowledge, it is expected that, using oral delivery methods, a patient will typically receive an oral dose of between 50 and 1500 mg of mast cell stabilizer per day, preferably divided into at least two equal doses. When drug is administered nasally, it is expected that an amount of between 5 and 100 mg of stabilizer will be administered each day, again with this amount being divided into several equal doses.

E. Comments Regarding Diabetes

Although the experiments described herein are concerned primarily with obesity, certain aspects suggest that the same methods could also be applied to treatment or prevention of type 1 diabetes. The therapeutic objective in treating diabetics would be to reduce or eliminate insulin dependence. The preferred drugs and dosages are the same as for obesity.

F. Packaging of Therapeutic Compositions

As described previously, the pharmaceutical compositions containing mast cell stabilizers may be placed in a finished pharmaceutical container and sold along with instructions to physicians regarding the use of the compositions. In the case of preparations for nasal delivery, the pharmaceutical composition will typically be a solution or powder packaged in a device designed for delivering the composition as a spray. Any of the devices known in the art for delivering drugs in this manner are compatible with the present invention. Depending upon the intended route of delivery, other containers may include bottles, vials, ampoules, blister packs etc.

Instructions concerning the use of pharmaceutical compositions may be included on the container with the pharmaceutical composition or as a package insert. Alternatively, the instructions may be included on a box or other package in which the pharmaceutical composition is sold. In all cases, the instructions will indicate that the pharmaceutical compositions are to be administered for the purpose of promoting weight loss or preventing weight gain. A description of the active ingredient(s) will also be included along with information concerning dosage and how the pharmaceutical composition should be administered.

G. Assay Methods

The invention also includes methods for evaluating the potential use of a compound in the treatment or prevention of obesity based upon its ability to stabilize mast cells. These assays are well known in the art and have been used in conjunction with the identification of agents useful in treating allergies.

One example of an appropriate assay that may be used is described in U.S. Pat. No. 6,225,327. Briefly, mast cells (about 5,000 per assay tube) are incubated at 37° C. for about 15 minutes with the test compound and then exposed to anti-human IgE (about 10 micrograms/ml). After an additional 15 minutes, reactions are terminated by centrifugation. Supernatants are then collected and analyzed for histamine content, e.g., by radioimmunoassay. A comparison is then made between the amount of histamine present in this sample (the "test sample") and the amount in a control preparation obtained by incubating mast cells and anti-human IgE in the absence of test compound. A reduction in histamine content in the test sample as compared to the control is an indication that the test compound is acting to stabilize the mast cells. The effectiveness of a stabilizer will be reflected by the concentration needed to achieve a given level of inhibition, e.g., a 50% reduction in histamine release.

EXAMPLES

This study demonstrates that mast cells contribute importantly to diet-induced obesity and diabetes. White adipose tissues (WAT) from obese humans and mice contain more mast cells than WAT from their lean counterparts. Genetically-determined mast cell deficiency and pharmacological stabilization of mast cells in mice reduce body weight gain and levels of inflammatory cytokines, chemokine, and proteases in serum and/or WAT, in concert with improved glucose homeostasis and energy expenditure. Mechanistic studies reveal that mast cells enhance WAT and muscle angiogenesis and associated adipogenesis-pertinent cathepsin activity. Consistent with reduced body weight gain and improved glucose tolerance, mast cell deficiency and stabilization increase levels of anti-adipogenic matrix fibronectin, glucose transporter Glut4, and insulin receptors in muscle and WAT. The use of cytokine-deficient mast cells established that these cells induce mouse adipocyte lipid deposition and cathepsin expression in vitro and promote diet-induced obesity and glucose metabolism in vivo by production of IL6 and IFN-γ. A mast cell stabilizing agent in clinical use reduced obesity and diabetes in mice, suggesting novel therapies for these common human metabolic disorders.

I. Methods

Mice

Wild-type (C57BL/6), Il6$^{-/-}$ (C57BL/6, N11), and Ifng$^{-/-}$ (C57BL/6, N10) mice were purchased from the Jackson Laboratories (Bar Harbor, Me.). Congenic Tnf$^{-/-}$ (C56BL/6, N10) and mast cell-deficient Kit$^{W-sh/W-sh}$ (C57BL/6, N>10) mice were generated by back-crossing to the C57BL/6 background as described (Sun, et al. *Nat. Med.* 13:719-724 (2007); Wolters, et al., *Clin Exp Allergy* 35:82-88 (2005)). The standing committee of Harvard Medical School approved all animal research protocols, and all mice were housed in a pathogen-free facility. To induce obesity, we fed 6-week-old mice (females and males) a Western diet (Research Diet, New Brunswick, N.J.) for 12-20 weeks. Mouse body weight was monitored weekly. By the end of each course of Western diet consumption, we performed glucose tolerance and energy expenditure assays as reported previously (Yang, et al., *Nat. Cell Biol.* 9:970-977 (2007)). Mouse blood samples were collected for serum adipokine measurement. Subcutaneous, visceral, and brown fat and skeletal muscle were harvested individually for protein extraction and paraffin section preparation. Tissue protein extracts were used for ELISA, immunoblot analysis, and cysteinyl cathepsin active site labeling. For immunoblot analysis, 30 µg of proteins were separated on an 8% SDS-PAGE to detect 220 kDa fibronectin (mouse monoclonal, 1:100, NeoMarkers, Fremont, Calif.) and 200 kDa insulin receptor (mouse monoclonal, 1:100, Calbiochem, San Diego, Calif.) or a 12% SDS-PAGE to detect Glut4 (mouse monoclonal, 1:200, R&D Systems, Minneapolis, Minn.), UCP1 (rabbit polyclonal, 1:3000, Abcam, Cambridge, Mass.), actin (mouse monoclonal, 1:500, Abeam), and glyceraldehyde-3-phosphate dehydrogenase (GAPDH, rabbit polyclonal, 1:1000, Santa Cruz Biotechnolog, Santa Cruz, Calif.). For cathepsin active site labeling, 30 µg of proteins were incubated with 1 µl of 600 mM dithiothreitol and 1 µl of [$^{125}$I]-JPM in a pH5.5 buffer as previously described. After incubating the reaction mixture at 37° C. for 1 hour, labeled proteins were separated on a 12% SDS-PAGE. Gel was stained with Coomassie blue, destained, dried, and exposed to an x-ray film. The liver and GI tract were harvested for histologic analysis.

Patient Selection

This study enrolled 80 obese subjects (mean age 37.5 years, range 20-66; mean BMI 48.5 kg/m$^2$, range 32-85; female/male ratio 69/11), prospectively recruited between 2003 and 2007 at the Department of Nutrition of Hôtel-Dieu Hospital (Reference Center for the Medical and Surgical Care of Obesity, Paris, France). The subjects were candidates for either a dietary intervention or gastric surgery in a clinical investigation program supported by Assistance Publique-Hôpitaux de Paris. Those with evidence of inflammatory or infectious diseases, cancer, alcohol abuse, or kidney disease were excluded. At the time of the gastric surgery, we obtained subcutaneous adipose tissue from the periumbilical area in a subset of the obese subjects (N=6, BMI=51.71±1.40 kg/m$^2$, glucose: 5.38±0.13 mmol/l, insulin: 13.32±1.06 μU/ml). Healthy, non-obese, age-matched (P=0.2) individuals (N=32, mean age 41.4 years, range 20-62; mean BMI 22.8 kg/m2, range 19.9-28.4; female/male ratio 22/10) living in the same geographic area were recruited as controls. In 10 lean controls (BMI=23.67±0.48 kg/m2, glucose: 4.82±0.45 mmol/l, insulin: 7.20±1.56 μU/ml), we obtained subcutaneous adipose tissue in the periumbilical area by needle biopsy. The volunteers participating in the metabolic exploration were weight-stable 3 months prior to the intervention. Blood samples and serum obtained in the morning after fasting were frozen at −80° C. until use. Tissue samples were processed for formalin fixation and paraffin embedding. The Ethics Committees of the Hôtel-Dieu Hospital approved the clinical investigations, and all subjects gave a written informed consent.

Immunohistology

Human and mouse WAT and muscle tissues were fixed with 10% formalin overnight and embedded in paraffin, from which 5 μm sections were prepared. Anti-human mast cell tryptase (mouse monoclonal, 1:100, Dako, TRAPPES CEDEX, France), anti-mouse mast cell CD117 (rat monoclonal, 1:10, eBiosciences, Inc., San Diego, Calif.), and anti-mouse CD31 (rat monoclonal, 1:400, Pharmingen, San Diego, Calif.) immunostained for mast cells and microvessels on WAT, muscle, and liver sections. Researchers blinded to the origin of tissue counted human tryptase-positive and CD117-positive mast cells, and data are presented as cell numbers per mm$^2$. CD31-positive areas in WAT and muscle were determined using Image-Pro Plus software as described, and data were presented as percentage of CD31-positive areas (Wang, et al., *J. Biol. Chem.* 281:6020-6029 (2006); Wild, *Microvasc Res.* 59:368-376 (2000)). Hematoxylin and eosin staining assisted histologic assessment of the GI tract.

ELISA

Frozen mouse WAT was pulverized and lysed in a RIPA buffer (Pierce, Rockford, Ill.) containing a protease inhibitor cocktail (Calbiochem, San Diego, Calif.). Both WAT and serum samples were subjected to ELISA analysis for IL6 (BD Biosciences), TNF-α (PeproTech, Rocky Hill, N.J.), IFN-γ (PeproTech), MCP-1 (PeproTech), adiponectin (R&D Systems), MMP-9 (R&D Systems), CatS (R&D Systems), and CatL (Bender MedSystems Inc, Burlingame, Calif.) according to manufacturers' instructions.

To measure human serum tryptase levels, a 96-well plate was pre-coated with a rabbit anti-human tryptase polyclonal antibody (1:1000, Calbiochem). Diluted human serum samples (1:2) along with recombinant human tryptase as standard were added to antibody-coated plate. After 2 hours incubation at room temperature, plate was washed and incubated for 1 hour with an anti-human tryptase monoclonal antibody (1:2000, AbD Serotec, Raleigh, N.C.). HRP-conjugated anti-mouse IgG (1:1000, Thermo scientific, Waltham, Mass.) was used as detecting antibody.

3T3-L1 Cell Culture and Differentiation

Mouse pre-adipocyte 3T3-L1 (The American Type Culture Collection, Manassas, Va.) were cultured and differentiated into adipocytes in insulin, dexamethasone, and isobutylmethylxanthine on 6-well or 24-well plates as described (Yang, et al., *Nat. Cell Biol.* 9:970-977 (2007)). To assess the role of mast cells in 3T3-L1 differentiation, we added either live mast cells (2×10$^6$ cells/well for 6-well plates or 5×05 cell/well for 24-well plates) or their degranulated protein extract (equivalent to the live cell numbers) into 100% confluent 3T3-L1 cells. Co-cultures were maintained for 7~9 days, and culture media with live mast cells or mast cell protein extracts were replaced every two days. Oil-red O staining quantified lipid deposition, and data were presented as $OD_{510nm}$ readings. Differentiated 3T3-L1 cells were also used for cathepsin active site labeling by lysing cells into a pH5.5 buffer as described (Shi, et al., *J. Biol. Chem.* 267:7258-7262 (1992)).

BMMC Culture and Reconstitution

BMMC were prepared from bone marrow from WT, $Il6^{-/-}$, $Tnf^{-/-}$, and $Ifng^{-/-}$ mice as we reported previously (Sun, et al. *Nat. Med.* 13:719-724 (2007); Sun, et al., *J. Clin. Invest.* 117:3359-3368 (2007)). After 5 weeks of differentiation in recombinant mouse IL3 (PeproTech) and stem cell factor (PeproTech) (Sun, et al. *Nat. Med.* 13:719-724 (2007)) cell purity and morphology were verified with CD117-mediated FACS analysis and toluidine blue staining, respectively. To examine the role of mast cells in obesity in mice, we injected BMMC (1×10$^7$/mouse) from each type of mouse to the tail vein of 6-week-old male $Kit^{W-sh/W-sh}$ mice. Two weeks after BMMC reconstitution, mice consumed a Western diet to induce obesity and diabetes. Mouse body weight was recorded weekly, and glucose tolerance assay was performed before harvesting the WAT for protein extract preparation.

Statistics

All data from mice were expressed as mean±SEM, and statistical significance was determined using a non-parametric Mann-Whitney test due to our small data size and abnormal data distribution. Human serum chymase and tryptase data are expressed as mean±SEM. The Shapiro-Wilcoxon test gauged the Gaussian distribution of all clinical and biological parameters. Skewed variables (chymase and tryptase levels) were log-transformed and verified to normalize their distribution before statistical analyses. Student's t test, analysis of variance (ANOVA), and Chi-square test for non-continuous values were used for comparisons between groups. Statistical analysis was performed with JMP statistics software (SAS Institute Inc., Cary, N.C.). P<0.05 was considered significant.

II. Results

In addition to adipocytes, WAT in obese subjects contain macrophages and lymphocytes (Weisberg, et al., *J. Clin. Invest.* 112:1796-1808 (2003); Wu, et al., *Circulation* 115: 1029-1038 (2007)). These inflammatory cells furnish cytokines, growth factors, chemokines, and proteases in WAT (Wu, et al., *Circulation* 115:1029-1038 (2007); Fantuzzi, *J. Allergy Clin. Immunol.* 115:911-919 (2005)). However, the role of these cells in the pathogenesis of obesity and associated metabolic complications diabetes remains uncertain. Other unrecognized cells may also contribute critically. Immunostaining of human adipose tissue sections with a mast cell-specific tryptase monoclonal antibody revealed increased numbers of mast cells in WAT from obese subjects compared with those from lean donors. Higher levels of mast cell proteases in the sera of obese donors accompanied this higher mast cell content. Using ELISA, we detected that obese donors (body mass index: BMI≧30 kg/mm$^2$) had significantly higher serum tryptase levels than lean subjects (BMI<30 kg/mm$^2$) before (P<0.01) and after adjusting for gender (P<0.01, multivariate analysis). These observations suggest a role for mast cells in obesity.

To assess the direct participation of mast cells in obesity, we studied mast cell-deficient $Kit^{W-sh/W-sh}$ mice in diet-induced obesity. While $Kit^{W-sh/W-sh}$ mice lack mature mast cells due to an inversion mutation of the c-Kit promoter region (Duttlinger, et al., *Proc. Nat'l Acad. Sci. USA* 92:3754-3758 (1995)), numbers and activities of other leukocytes in blood are normal, permitting probing of mast cell functions in vivo. Six-week-old male $Kit^{W-sh/W-sh}$ mice fed a Western diet for 12 weeks gained significantly less body weight than wild-type (WT) congenic controls. Similarly, WT mice receiving a daily intraperitoneal (i.p.) injection of the mast cell stabilizer disodium cromoglycate (DSCG) (Eigen, et al., *J. Allergy Clin. Immunol.* 80:612-621 (1987)) also had attenuated body weight gain. DSCG treatment did not further affect the body weight of the $Kit^{W-sh/W-sh}$ mice, suggesting it acted through mast cells. Consistent with reduced body weight, male $Kit^{W-sh/W-sh}$ mice or those receiving DSCG had significantly less total subcutaneous and visceral fat than untreated WT controls. Female $Kit^{W-sh/W-sh}$ or DSCG-treated WT mice exhibited similar reductions in body weight gain and subcutaneous and visceral fat. Like human adipose tissues, WAT from diet-induced obese mice also contain high numbers of c-Kit (CD117)-positive mast cells, whereas WAT from chow diet-fed lean mice had many fewer mast cells. Interestingly, WAT from DSCG-treated mice had mast cell numbers similar to WAT from untreated mice under the same dietary conditions, although these mice responded similarly to $Kit^{W-sh/W-sh}$ mice regarding body weight gain, suggesting that DSCG-treated WT mice had fewer active mast cells than untreated WT mice. Consistent with reduced body weight in male and female $Kit^{W-sh/W-sh}$ mice or those receiving DSCG, these mice also had significantly lower levels of serum leptin levels than WT controls. Not only were $Kit^{W-sh/W-sh}$ and DSCG-treated mice leaner but they also demonstrated more sensitivity to a glucose load. A glucose tolerance assay revealed significantly improved glucose tolerance in mice without mast cells ($Kit^{W-sh/W-sh}$) or with stabilized mast cells (WT treated with DSCG). To understand the mechanisms of these salutary effects of mast cell deficiency or inactivation, we performed energy expenditure assays and measured brown fat uncoupled protein-1 (UCP1). By measuring food/water intake, fecal/urine production, and $O_2$ consumption and $CO_2$ production, we found that $Kit^{W-sh/W-sh}$ mice and DSCG-treated WT mice had an increased resting metabolic rate, illustrated by significantly more $O_2$ consumption and $CO_2$ production than untreated WT mice. $Kit^{W-sh/W-sh}$ mice and those receiving DSCG had obviously higher brown fat UCP1 expression, a marker of energy expenditure, than WT control mice. Importantly, neither reduced food/water intake nor any toxic effect of DSCG caused the decreased body weight and improved glucose tolerance in DSCG-treated WT mice. Histological analysis demonstrated that the livers and gastrointestinal (GI) tracts of DSCG-treated Western diet-fed mice did not differ pathologically from those of chow diet-fed WT mice. While abundant mast cells and adipocytes appeared in the fatty livers from Western diet-fed WT mice, we did not detect mast cells or lipid-loaded adipocytes in livers from chow diet-fed WT or Western diet-fed WT mice treated with DSCG. Similarly, histological examination of the pancreas, stomach, colon, and small intestine exhibited no gross differences between chow diet-fed WT and Western diet-fed DSCG-treated WT mice. To extend our observations, we fed WT mice a Western diet for 12 weeks to produce obesity and diabetes, and grouped these obese and diabetic mice into four treatment groups: I, continued feeding with a Western diet; II, switched to a chow diet; III, continued feeding with a Western diet together with a daily i.p. injection of DSCG; IV, switched to a chow diet and treated with DSCG. Although a change of the diet (group II) also reduced body weight (8%) and improved glucose tolerance as expected, a combination of diet change and DSCG administration (group IV) yielded the greatest improvement of both body weight and glucose tolerance. Eight weeks after DSCG treatment, the body weight of group III mice decreased by 12%, but that of group IV mice decreased by 19% and stabilized around 40~41 grams. Importantly, group IV mice also demonstrated the highest glucose tolerance among the four groups, suggesting the possibility of managing human obesity and diabetes by stabilizing mast cells.

III. Discussion

The development of obesity involves adipogenesis, angiogenesis, and matrix remodeling. Angiogenesis holds particular importance in obesity. Besides providing the WAT with nutrients, microvessels also provide a path for leukocyte infiltration followed by adipokine release. Inhibition of angiogenesis blocks adipose tissue development in mice (Rupnick, et al., *Proc. Natl. Acad. Sci. USA* 99:10730-10735 (2002)). WAT and muscle tissue from obese WT mice showed substantial immunostaining for the endothelial cell marker CD31. In contrast, Western diet-fed $Kit^{W-sh/W-sh}$ mice or those receiving DSCG had CD31-positive areas similar to those from chow diet-fed lean mice. Reduced angiogenesis may impair leukocyte infiltration and therefore reduce WAT production of inflammatory mediators (Skoura, et al., *J. Clin. Invest.* 117:2506-2516 (2007)). Consistent with this notion, $Kit^{W-sh/W-sh}$ mice or those receiving DSCG had lower levels of IL6, TNF-α, IFN-γ, MCP-1, matrix metalloprotease-9 (MMP-9), and cathepsin S (CatS) in serum and/or WAT, although some adipokines (e.g., adiponectin and CatL) did not change significantly. Matrix proteolysis may contribute to angiogenesis by releasing pro-angiogenic peptides (Xu, et al., *J. Cell Biol.* 154:1069-1079 (2001)). We have previously shown that CatS plays a critical role in angiogenesis by degrading anti-angiogenic peptides and generating pro-angiogenic lamin-5 fragment γ2 (Wang, et al., *J. Biol. Chem.* 281:6020-6029 (2006)). Reduced angiogenesis in $Kit^{W-sh/W-sh}$ and DSCG-treated mice accompanied low CatS levels in WAT and serum. After incubating WAT protein extracts with $[^{125}I]$-JPM, which selectively labels active cathepsins, we found impaired active cathepsins, including CatS, CatK, and CatB in $Kit^{W-sh/W-sh}$ WAT. Interestingly, WAT from DSCG-treated mice still had levels of active CatS and CatK similar to WT controls, consistent with the observation of high numbers of mast cells in these tissues. CatS ELISA allowed us to determine local and systemic levels among different mice. Similar to the observations from the JPM labeling experiment, both male and female $Kit^{W-sh/W-sh}$ mice exhibited lower serum and WAT CatS levels than the WT controls. In contrast, DSCG treatment reduced significantly the CatS levels in serum but not in WAT extracts, suggesting that this anti-allergy agent effectively inactivated mast cells.

Our previous studies suggest that cysteinyl cathepsins not only promote angiogenesis but also participate in adipogenesis by degrading the anti-adipogenic matrix constituent fibronectin, the glucose transporter Glut4, and the insulin receptor (IR) (Wang, et al., *J Biol. Chem.* 281:6020-6029 (2006); Yang, et al., *Nat. Cell Biol.* 9:970-977 (2007); Taleb, et al., *Endocrinology* 147:4950-4959 (2006)). Deficiency and inactivation of mast cells may indirectly affect these proteins due to reduced cathepsin activity. In agreement with this hypothesis, all three molecules were increased in WAT and muscle from $Kit^{W-sh/W-sh}$ mice. Interestingly, we detected more fibronectin, Glut4 and IR molecules in WAT and muscle from DSCG-treated mice than $Kit^{W-sh/W-sh}$ mice, suggesting that DSCG affected more than mast cells. However, such additional effects of DSCG did not further change the body weight gain and glucose tolerance in Kit$^{W\text{-}sh/W\text{-}sh}$ mice or the histology of the liver and the GI tract in WT mice.

To understand further the molecular mechanism by which mast cells control Murine obesity and diabetes, we prepared bone marrow-derived mast cells (BMMC) from mice that lacked one of three common mast cell cytokines (IL6, TNF-α, and IFN-γ) and examined whether absence of any of these cytokines impaired mast cell activity in inducing preadipocyte differentiation in vitro and diet-induced obesity and diabetes in vivo. BMMC from WT, Tnf$^{-/-}$, and Ifng$^{-/-}$ mice induced 3T3-L1 adipogenesis and associated cathepsin expression even without differentiation cocktails (insulin, dexamethasone, isobutylmethylxanthine), though the underlying mechanisms remain unknown. In contrast, Il6$^{-/-}$ BMMC had much less potency on both variables. To prove that these mast cell cytokines play a role in obesity in vivo, we adoptively transferred these cells to male Kit$^{W\text{-}sh/W\text{-}sh}$ mice. After 13 weeks on a Western diet, mice reconstituted with WT and Tnf$^{-/-}$ BMMC but not Il6$^{-/-}$ and Ifng$^{-/-}$ BMMC gained significantly more body weight than non-reconstituted mice, although they were all leaner than WT controls. Consistent with the body weight differences, those receiving WT and Tnf$^{-/-}$ BMMC had significantly higher serum insulin and glucose levels than non-reconstituted mice or those receiving Il6$^{-/-}$ and Ifng$^{-/-}$ BMMC. Kit$^{W\text{-}sh/W\text{-}sh}$ mice that received Il6$^{-/-}$ and Ifng$^{-/-}$ BMMC but not WT or Tnf$^{-/-}$ BMMC also demonstrated improved glucose tolerance compared with WT controls, suggesting that mast cell-derived IL6 and IFN-γ contribute to these metabolic derangements. In support of this conclusion, we detected higher amounts of matrix fibronectin, Glut4, and IR in WAT extract from Il6$^{-/-}$ and Ifng$^{-/-}$ BMMC-reconstituted Kit$^{W\text{-}sh/W\text{-}sh}$ mice than WT mice or those receiving WT or Tnf$^{-/-}$ BMMC. Differences of these molecules in WAT may result from altered proteolysis or differences in adipocyte size. Although we found smaller WAT adipocytes from Kit$^{W\text{-}sh/W\text{-}sh}$ mice than WT controls, WAT adipocyte sizes did not vary significantly between different BMMC-reconstituted mice. In contrast, the various reconstituted recipients had clear differences in cysteinyl cathepsin expression. It is unknown why Ifng$^{-/-}$ BMMC induced 3T3-L1 adipogenesis and cathepsin activities equally well as WT BMMC but failed to restore body weight and glucose sensitivity. Mast cell-derived IFN-γ may affect other processes in addition to adipocyte differentiation, such as angiogenesis or protease expression in neighboring cells by a paracrine effect. The observation of low cathepsin activity in WAT from Ifng$^{-/-}$ BMMC-reconstituted Kit$^{W\text{-}sh/W\text{-}sh}$ mice supported this notion. Therefore, how mast cell mediators regulate WAT growth in vivo and which additional mast cell factors participate merit further investigation.

This study establishes a novel role of mast cells in Murine obesity and diabetes and suggests potential new therapies for these common human metabolic diseases using anti-allergy drugs in common clinical use.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of inhibiting weight gain in an obese patient, comprising administering to said patient an effective amount of a drug selected from the group consisting of cromolyn and ketotifen, wherein the patient is free of allergies, heart disease and diabetes at the time that the administration of the drug is initiated.

2. The method of claim 1, wherein said drug is cromolyn and is administered orally at a dose of 50-1500 mg per day.

3. The method of claim 1, wherein said drug is cromolyn and is administered nasally at a dose of 5-100 mg per day.

4. The method of claim 1, wherein said drug is cromolyn sodium or cromolyn disodium administered orally at a dose of 200-1000 mg per day.

5. The method of claim 1, wherein said drug is ketotifen and is administered orally at a dose of 50-1500 mg per day.

6. The method of claim 1, wherein said drug is ketotifen and is administered nasally at a dose of 50-100 mg per day.

* * * * *